(12) United States Patent
Marquis

(10) Patent No.: US 8,409,095 B1
(45) Date of Patent: Apr. 2, 2013

(54) SYSTEMS AND METHODS FOR HANDS FREE CONTROL OF MEDICAL DEVICES

(75) Inventor: Steven Russel Marquis, Fall City, WA (US)

(73) Assignee: SonoSite, Inc., Bothell, WA (US)

( * ) Notice: Subject to any disclaimer, the term of this patent is extended or adjusted under 35 U.S.C. 154(b) by 497 days.

(21) Appl. No.: 12/553,868

(22) Filed: Sep. 3, 2009

(51) Int. Cl.
*A61B 5/00* (2006.01)
(52) U.S. Cl. ............ 600/437; 600/443; 600/459; 73/584
(58) Field of Classification Search .................. 600/437, 600/459; 73/584
See application file for complete search history.

(56) References Cited

U.S. PATENT DOCUMENTS

| | | | | |
|---|---|---|---|---|
| 5,977,878 A | * | 11/1999 | Lang | 340/815.4 |
| 6,595,924 B2 | * | 7/2003 | Kawae et al. | 600/437 |
| 7,127,401 B2 | * | 10/2006 | Miller | 600/437 |
| 2009/0054781 A1 | * | 2/2009 | Stonefield et al. | 600/459 |

* cited by examiner

*Primary Examiner* — Brian Casler
*Assistant Examiner* — Phong K Huynh

(57) ABSTRACT

A medical device includes a control interface for operating the medical device in a hands-free mode. To control the medical device in a hands-free mode, the control interface includes multiple proximity sensors, each sensor associated with a level of adjustment. For example, a sensor located on a top portion of the medical device is used to increase the level of adjustment. And similarly, a sensor located on a bottom portion of the medical device is used to decrease the level of adjustment. The magnitude of the level of adjustment applied to a parameter of the medical device is controlled based at least in part on the length of time an object remains in proximity to a respective sensor. In one embodiment, the longer the object is held over a respective sensor the more adjustment the control interface will make to the parameter.

15 Claims, 3 Drawing Sheets

SYSTEMS AND METHODS FOR HANDS FREE CONTROL OF MEDICAL DEVICES

CROSS-REFERENCE TO RELATED APPLICATIONS

This application is related to concurrently filed, co-pending, and commonly assigned U.S. application Ser. No. 12/553,846, entitled "SYSTEMS AND METHODS FOR ENHANCEMENT OF MEDICAL DEVICE TRACKING," which filed on Sep. 3, 2009, is incorporated by reference in its entirety.

TECHNICAL FIELD

This disclosure is related to medical device controls and more specifically to systems and methods for controlling electronic medical devices in a sterile environment.

BACKGROUND OF THE INVENTION

The use of electronic medical devices of all types is now routine. Often these devices are used in environments where adjustments must be made during the course of a medical procedure. In many situations, these adjustments need to be made to a control, or set of controls that may be preferably remotely located from the operator.

By way of example, a sonographic procedure is performed by a sonographer holding a scan-head probe against a patient's body and moving the probe along the body's contours in order to facilitate obtaining the desired image. While the sonographer is moving the probe with one hand it is often necessary to make one or more adjustments with respect to controls located on a control panel located separately from the probe. Typically, the sonographer must stretch spread-eagle style to reach both the control panel and the patient at the same time.

In some situations, remote control buttons can be placed on the probe to avoid requiring the operator to reach one hand for controls mounted behind or off to the side of the location where the probe is being used. However, in the case of a sterile environment the operator must not touch any non-sterile controls. This then presents a problem when any adjustments must be made during the course of the procedure.

BRIEF SUMMARY OF THE INVENTION

If simple control of a key parameter is needed, by incorporating a presence detector at the top of a control unit and one at the bottom of the control unit, the operator need only waive a hand near one or the other of the embedded detectors to control an up or down setting of a medical device. In one embodiment, the longer the hand is held over a detector the more adjustment the system will make. In another embodiment, safety mechanisms protect against false readings, for example, by not reacting when both detectors concurrently sense a presence.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is made to the following descriptions taken in conjunction with the accompanying drawing, in which.

DETAILED DESCRIPTION OF THE INVENTION

Figure 1:
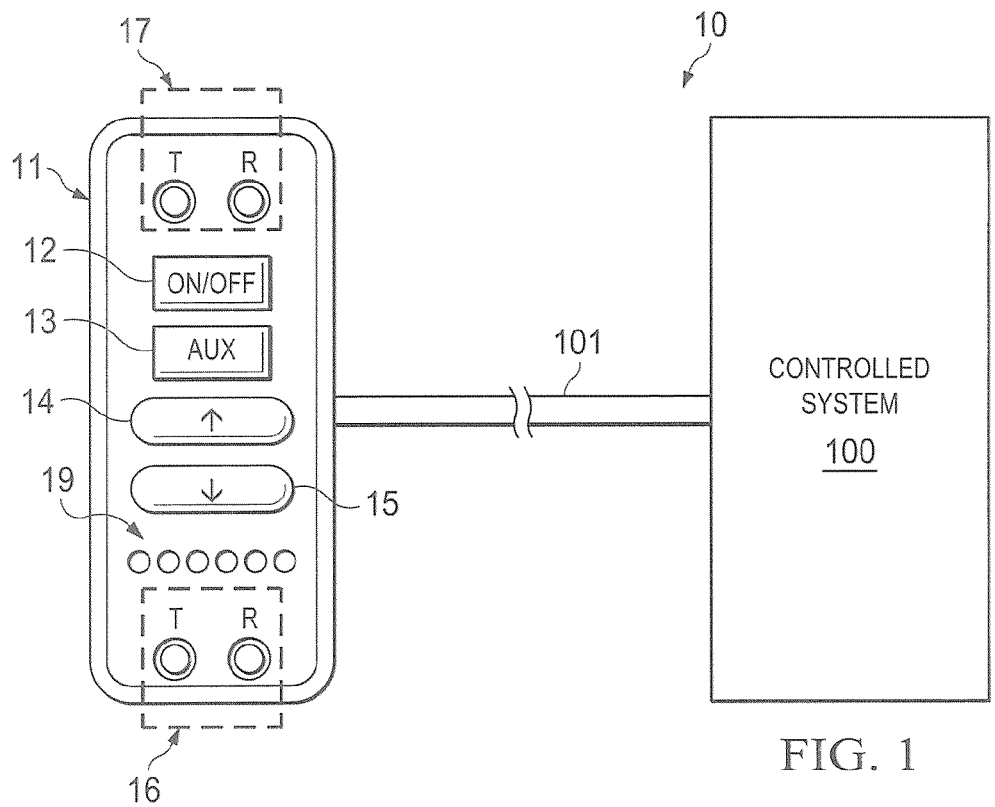
FIG. 1 shows one embodiment of a medical device employing the concepts of the invention.

FIG. 1 shows one embodiment of medical device 10 having control interface 11 and controlled system 100 employing the concepts of the invention. In the embodiment shown, the system is turned on by the operator pushing button 12 of control interface 11. Control interface 11 is connected, usually by a cable, such as cable 101 or possibly via RF link, such as Bluetooth™, to a controlled system, such as system 100. The control interface 11 may be attached to the controlled system 100 or physically separated therefrom as shown. Control interface 11 can be a remote control of a device or embedded in the device itself. Controlled system 100, when used for sonographic procedures could be as shown in the '363 patent or any other sonographic control system. Note that these are only examples and the inventive concepts can be used with any type of system that requires an operator to change parameters without making physical contact with a control circuit.

By way of example; to control the level of some parameter, up or down, such as a light on the end of a catheter, auxiliary control button 13 can be used to turn on/off the light (or turn on/off other equipment). In such a situation the power (or other parameter) of the light (or other equipment) can be controlled by increase or decrease buttons 14 and 15, respectively. If the operator desires to work in the hands-free mode then that mode is entered, for example, by operating both buttons 14 and 15 simultaneously.

Note that if the hand-free mode needed to be enabled without physically touching on/off switch 12 then proximity detectors 16 and 17 could be used, for example by moving an object, such as a hand or a sterile cloth, simultaneously or in some sequence into proximity with both of them for a period of time.

Once the hands-free mode is entered, the operator simply moves an object, such as a hand, into proximity with top sensor 17 when power is to be increased or into proximity with lower sensor 16 when power is to be decreased. Because the sensors are located top and bottom the direction of power change is intuitive for the operator. The length of time the object is maintained in proximity to the respective sensor determines the magnitude of the change. Alternatively, a wave of the hand could be used to signal the controller that a new incremental step up or down was requested.

In the embodiment illustrated, the actual sensors are within the housing of control interface 11 (as will be discussed with respect to FIG. 2) and their respective signals are presented to the operator via holes (labeled T and R in FIG. 1).

In order to prevent false readings, control logic verifies that both sensors 16 and 17 are not receiving presence signals simultaneously (except perhaps prior to hands-free operation when simultaneous reception for a certain length of time could equate to a turn on signal). Holes T and R are designed in this embodiment to have a relatively narrow "field of view" so that they will only sense within a defined area. The volume of the presence sensing space (cone of acceptance) is a combination of hole placement, hole opening size, signal power and distance the actual sensor is placed behind the aperture. If desired, one or more of these variables can be operator controllable. For example, one or both of the T, R apertures can be made variable so that the operator can change the shape of the cone of acceptance to adjust distance/sensitivity as desired. The sensors can be made to be selectively sensitive to only a narrow spectrum such as infrared. The apertures would advantageously have covers on them that are transparent to the infrared region of light. The covers could also be filters to prevent other signal sources from interfering in the operation. The light source T can also be modulated such that sensor R is selective to only that modulation thereby making the detector especially resistant to false readings.

In a preferred embodiment a narrow cone of acceptance is desired. Also, we contemplate that the timing for power increase will be a level change for each second of detected presence, but again that is controllable. Power level display 19 can be used to show the operator the current level by progressively changing the lighted ones of the dots or, if desired, a digital numerical display could be used.

Note that the system as illustrated is designed for binary operation such that the object (hand) is either being sensed or not sensed and the time of presence determines the magnitude of the change. However, the system could also be designed such that the magnitude of the parameter to change is a function of the closeness of the hand to the sensor. In that instance, only one sensor might be necessarily employed.

Figure 2:
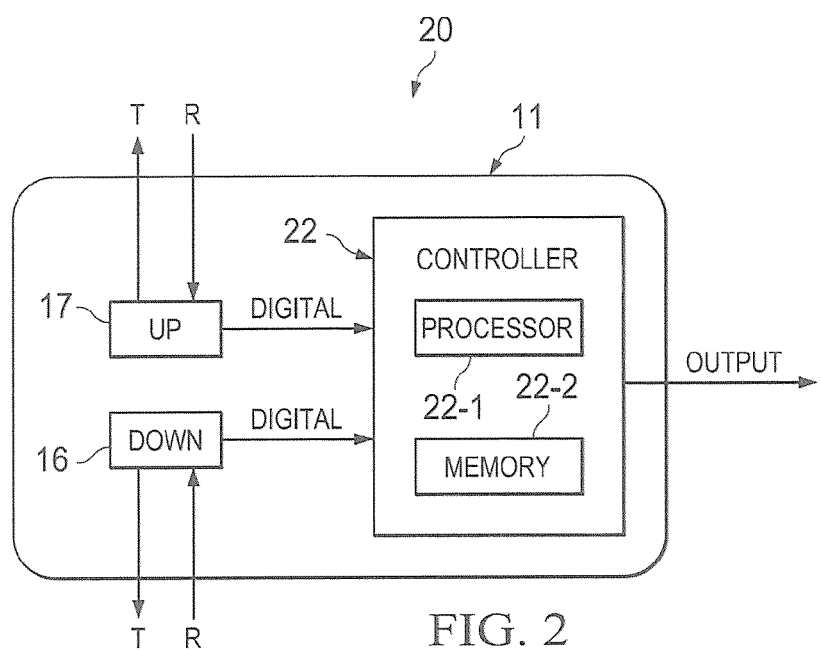
FIG. 2 illustrates one embodiment of a control system for using proximity detectors for controlling a medical device.

FIG. 2 illustrates one embodiment 20 of a control system for using proximity detectors for controlling the medical device shown in FIG. 1. Sensors 16 and 17 can have analog or digital outputs. Analog output sensor would be used, for example, if closeness to the sensor is to be used in the calculation. If closeness to the sensor were to be used to determine a magnitude change, having a second sensor, is especially helpful to help prevent a false reading from persons moving in proximity to the control interface. False readings are also minimized by a narrowly focused cone of acceptance (as discussed above) by controller 22. In the case of analog operation, the output is a numerical representation of the distance of the detected hand to the control interface. In the case of "digital", the output is binary, i.e., detected or not detected. Thus, in the case of a digital detector, the output from sensors 16 and 17 would be either a "1" or a "0".

Sensors 16 and 17 each send out a transmit signal which is preferably a modulated RF signal for more accurate presence detection. In the embodiment, the RF signal is transmitted using an infrared LED. When an object comes into the cone of acceptance, the modulated signal is reflected back to the respective R aperture (which need not be the same size as the transmit aperture) and sensor 16 or 17. The returning reflected signal is detected by an infrared detector and demodulated to determine if an object is within the zone of acceptance or not. In the case of a digital detector, if a threshold is exceeded, it provides a digital signal, usually a "1" to controller 22.

In one embodiment, sensors 16 and 17 can be GP2Y0A21YK (Analog type) or GP2Y0D21YK (Digital judgment type) obtained from Sharp Electronics Corporation. Note that the sensors can be any type of presence sensor, electromagnetic, ultrasound, unmodulated light, etc. Also note that while sensors 16 an 17 are paired on a single unit, there can be several different sensors and several different sensor types each controlling different functions or working in combination with each other to perform a single function with more accuracy.

As noted above, while the discussion centers on up/down control of a laser light, the system could also control up and down sensitivity or power or any other parameter of any type of medical device, including a power level (or formed beam direction control) of the probe itself.

The difference between analog and digital outputs from the sensor is that with digital the system need only detect presence or absence (1 or 0) and then make a decision about what one or the other means. In the case of the digital output, it is possible to set a detection threshold. Some sensors allow an iteratively adjustment and other devices are pre-set. Generally, close detection for a medical instrument is desired. For analog sensors the controller would interpret the actual voltage level in order to make the appropriate decisions.

Figure 3:
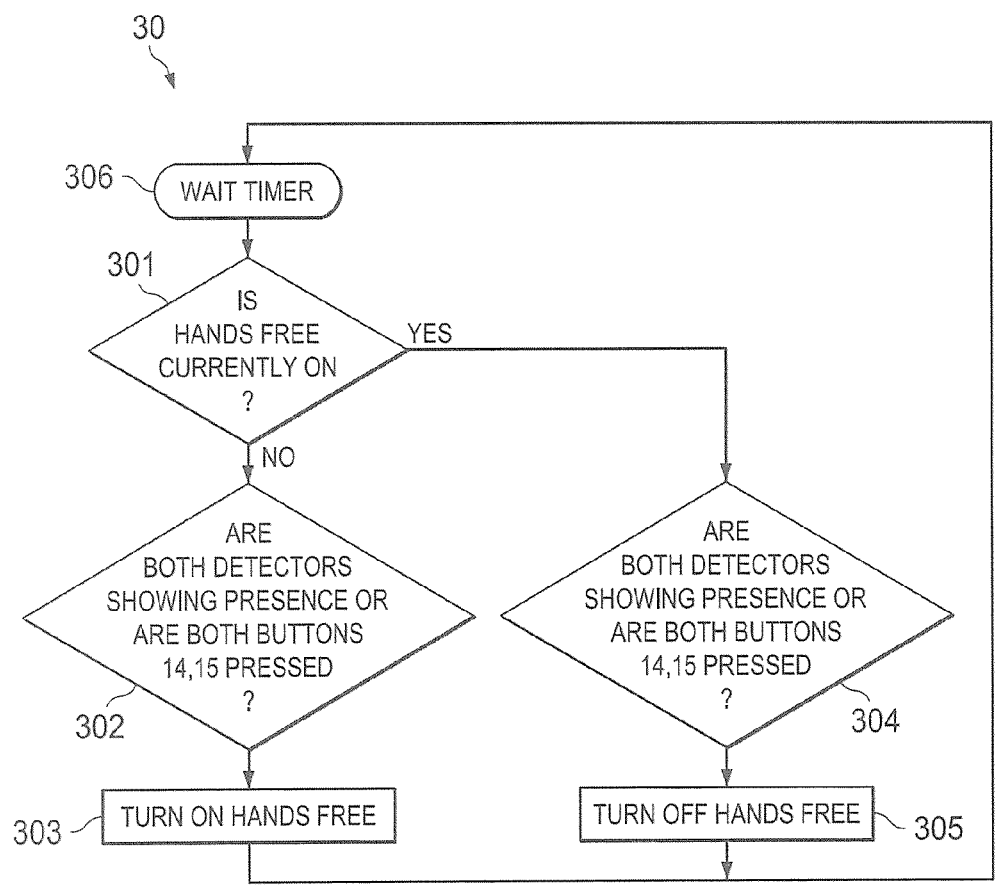
FIGS. 3 and 4 show embodiments of flow charts for controlling methods for utilization of proximity detectors.

FIG. 3 shows one embodiment 30 of a method for controlling the on/off of the hands-free operation for utilization of proximity detectors. The method illustrated in FIGS. 3 and 4 can be run on a processor, such as processor 22-1, (FIG. 2) in conjunction with memory 22-2 or it can be performed in hardware or in a combination of hardware and processor control.

Process 301, working in conjunction with wait timer 306, determines if the control interface is in the hand-free mode. If not, then the interface will not respond to the detection of presence at either sensor until the hand-free mode is activated. Activation can be by operation of a switch (such as switch 12, FIG. 1) or as shown by process 302 if desired where simultaneous presence detection from the "up" and "down" sensors is determined. If process 301 had determined the system had already been in the hands-free mode, then upon process 304 determining that both detectors or both up and down switches are activated, the system would leave the hands-free mode via process 305.

Figure 4:
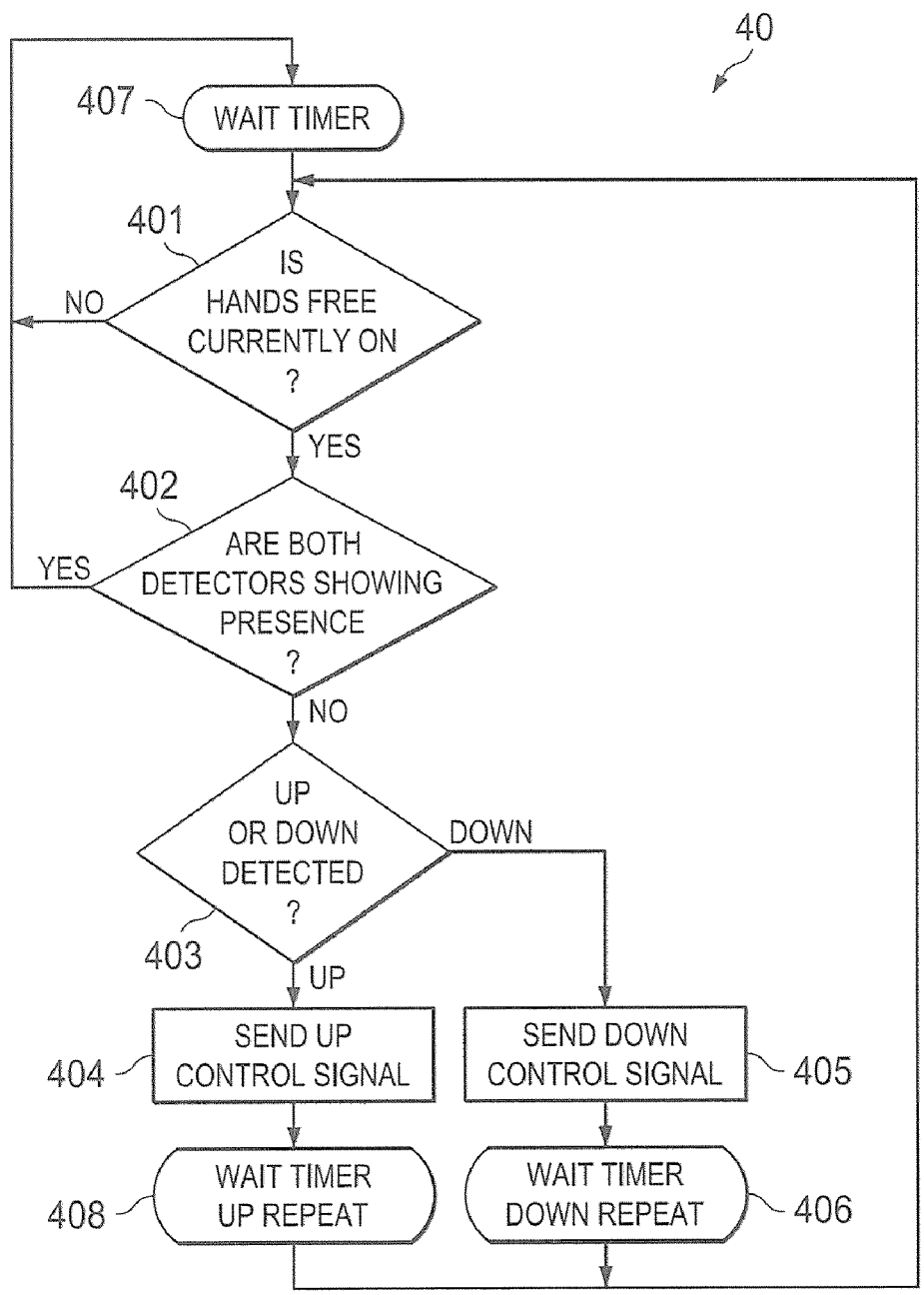

FIG. 4 shows one embodiment 40 of a method for controlling the up/down function of a controlled system by hands-free operation. Process 401 determines if the system is in the hands-free mode. If not, timer 407 waits for a period of time. When process 401 determines the system to be in the hands-free mode, process 402 determines if both sensors 16 and 17 are sending detection signals. If both detectors are doing so at the same time then this condition prevents both the up and down signals from being sent and timer 407 delays operation for a period of time, for example, two seconds.

Assuming now that an "up" presences has been detected alone, then process 403, in conjunction with process 404 sends an output control signal indicating that power should be raised (or indicating that some other function should be increased).

Following a wait period determined by timer 408 (for example, one second), the process repeats. If the up presence is still being detected, another up control signal is sent. This continues until process 403 no longer detects a presence at the up presence detector.

The down presence detector works similar to the up detector only using processes 403, 405 and 406.

Note that if desired the operator can have an input to change the up and down times (408, 406, respectively). Note also that wait timer 407 and the up and down times need not be the same time intervals.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A sonographic control system comprising:
   a control interface comprising a first and second sensor positioned at a first location and a second location of the control interface, respectively,
   wherein the first sensor is configured to detect an object being in proximity to the first sensor and to generate, responsive to detecting the object, a first control signal, the first control signal indicating an increased level of adjustment of a parameter of the sonographic system;
   wherein the second sensor is configured to detect the object being in proximity to the second sensor and to generate, responsive to detecting the object, a second control signal, the second control signal indicating a decreased level of adjustment of the parameter of the sonographic system; and
   a controller coupled to receive the first and second control signals, the controller configured to:
   initiate a hands-free operation of the sonographic system responsive to receiving the first and second control signals at the same time;
   generate, during the hands-free operation, an output signal to adjust the parameter of the sonographic system based at least in part on an increased or a decreased level of adjustment associated with the first control signal or the second control signal; and
   prohibit generation of the output signal to adjust the parameter of the sonographic system during hands-free operation responsive to receiving the first and the second control signal at the same time.

2. The sonographic control system of claim 1, wherein the first sensor is configured to generate the first control signal to increase a magnitude of the increased level of adjustment and the second sensor is configured to generate the second control signal to decrease a magnitude of the decreased level of adjustment, the magnitude of the increased and decreased level of adjustment being a function of length of time the object is within the proximity of the first or second sensor.

3. The sonographic control system of claim 1, wherein the first location is at a top portion of the control interface and the second location is at a bottom portion of the control interface.

4. The sonographic control system of claim 3 further comprising:
   means for preventing false control signals during hands-free operation of the sonographic system based on simultaneous detection of objects by the first and second sensors.

5. The sonographic control system of claim 1 wherein the sensors are configured to detect the object within a cone of acceptance away from a physical boundary of the control interface.

6. The sonographic control system of claim 5 wherein the sensors are configured such that the cone of acceptance is operator controlled.

7. The sonographic control system of claim 6 wherein each sensor comprises:
   a transmit infrared LED and a receive infrared detector.

8. The sonographic control system of claim 7 wherein signals applied to each the transmit LED are RF modulated.

9. A method of operating a sonographic system, the method comprising:
   determining if a first and a second sensor are sending a first and a second control signal, respectively, at the same time, the first and second control signal indicating one or more objects being in proximity to, but not touching, a top or a bottom sensor mounted within a sonographic control system;
   responsive to a determination that the first and second sensors are sending the first and second control signal at the same time, initiating hands-free operation of the sonographic system;
   during hands-free operation, receiving at a control circuit the first or second control signal; and
   adjusting a parameter of the sonographic system responsive to receiving the first control signal or the second control signal.

10. The method of claim 9 further comprising:
    prohibiting hands-free operation of the sonographic control system when the one or more objects are simultaneously detected at the first and second sensor.

11. The method of claim 9 wherein the sonographic control system is a hand-held device.

12. The method of claim 11 wherein an increased level control signal is signified by a proximity detection at the first sensor and a decreased level control signal is signified by a proximity detection at the second sensor, the first sensor corresponding to a top positioned sensor and the second sensor corresponding to a bottom positioned sensor.

13. The method of claim 12 further comprising:
    controlling a magnitude of the first and second control signal based on a time the one or more objects is within proximity to the first or second sensor, wherein proximity being defined as the one or more objects being within a cone of acceptance defined by each sensor.

14. The method of claim 13 wherein the cone of acceptance is defined by a RF modulated infrared signal generated at each sensor from within the hand-held device.

15. The method of claim 13 wherein further comprising:
    adjusting the cone of acceptance from time to time.

* * * * *